United States Patent
Mueller et al.

(10) Patent No.: US 9,550,588 B2
(45) Date of Patent: Jan. 24, 2017

(54) WELDING DEVICE, USE THEREOF AS A CONTROL VALVE, AND METERING DEVICE

(71) Applicant: Sartorius Lab Instruments GmbH & Co. KG, Goettingen (DE)

(72) Inventors: Michael Mueller, Goettingen (DE); Swen Weitemeier, Loedingsen (DE); Steffen Strietzel, Siemerode (DE)

(73) Assignee: Sartorius Lab Instruments GmbH & Co. KG, Goettingen (DE)

( * ) Notice: Subject to any disclaimer, the term of this patent is extended or adjusted under 35 U.S.C. 154(b) by 855 days.

(21) Appl. No.: 13/889,824

(22) Filed: May 8, 2013

(65) Prior Publication Data

US 2013/0312370 A1 Nov. 28, 2013

Related U.S. Application Data (63) Continuation of application No. PCT/EP2011/005155, filed on Oct. 14, 2011.

(30) Foreign Application Priority Data

Nov. 8, 2010 (DE) .................. 10 2010 060 401

(51) Int. Cl.
*B65B 3/28* (2006.01)
*G01G 17/06* (2006.01)
(Continued)

(52) U.S. Cl.
CPC .............. *B65B 3/28* (2013.01); *A61M 39/146* (2013.01); *A61M 39/18* (2013.01); *B29C 65/02* (2013.01);
(Continued)

(58) Field of Classification Search
CPC .............. B65B 3/003; B65B 3/10; B65B 3/12; B65B 3/16; B65B 3/26; B65B 3/28; B65B 3/36; B65B 7/14; B65B 39/005; B65B 51/14; B65B 51/142; B65B 51/303; B65B 57/145; A61M 39/146; A61M 39/28; A61M 2039/282; F16K 7/04; F16K 7/045; F16K 49/00–49/007; B29C 65/743; B29C 65/7451; B29C 66/4312; B29C 66/8491; B29C 66/857; B29C 66/91411; B29C 66/9241; B29C 66/92615; G01G 17/04; G01G 17/06

(Continued)

(56) References Cited

U.S. PATENT DOCUMENTS 3,491,503 A * 1/1970 Ashton et al. .......... B65B 55/10
                                                                141/1
3,788,374 A    1/1974 Saijo
(Continued)

FOREIGN PATENT DOCUMENTS

DE            1037355 B   *  8/1958  ............. B29C 65/04
DE   202007014392 U1    2/2008
(Continued)

OTHER PUBLICATIONS

JPO machine translation of JP 9-19495, retrieved Mar. 15, 2016, 3 pages.*

*Primary Examiner* — Stephen F Gerrity
(74) *Attorney, Agent, or Firm* — Edell, Shapiro & Finnan, LLC (57) ABSTRACT

A welding device for the sealing welding of thermopolastic hoses (184), includes a clamping device (12) with at least two clamping jaws (122, 124), of which at least one is movable and between which a hose (184) which is to be welded can be clamped, wherein the clamping device (12) has a heating devices (38; 40; 64) which is coupled to a control unit (30) and is configured to heat the hose clamped (Continued)

between the clamping jaws (122, 124). The invention is distinguished in that the at least one movable clamping jaw (122) is actuable with a controllable, bidirectional actuator (32, 34; 42-52; 54, 56, 58) which is coupled to the control unit (30) in such a manner that the clamping pressure acting on the hose (184) can be adjusted independently of the heating device.

9 Claims, 3 Drawing Sheets (51) Int. Cl.
| | |
|---|---|
| B65B 51/10 | (2006.01) |
| B65B 57/14 | (2006.01) |
| B65B 3/00 | (2006.01) |
| B29C 65/02 | (2006.01) |
| B29C 65/74 | (2006.01) |
| B29C 65/00 | (2006.01) |
| G01G 17/04 | (2006.01) |
| A61M 39/14 | (2006.01) |
| A61M 39/18 | (2006.01) |
| B65B 7/14 | (2006.01) |
| B29C 65/04 | (2006.01) |
| B29C 65/06 | (2006.01) |
| B29C 65/08 | (2006.01) |
| B29C 65/14 | (2006.01) |
| B29C 65/18 | (2006.01) |
| B29C 65/30 | (2006.01) |
| B29L 23/00 | (2006.01) |
| B29L 31/00 | (2006.01) |

(52) U.S. Cl.
CPC ......... *B29C 65/743* (2013.01); *B29C 65/7451* (2013.01); *B29C 66/1122* (2013.01); *B29C 66/4312* (2013.01); *B29C 66/7392* (2013.01); *B29C 66/81427* (2013.01); *B29C 66/8322* (2013.01); *B29C 66/8491* (2013.01); *B29C 66/857* (2013.01); *B29C 66/9161* (2013.01); *B29C 66/91411* (2013.01); *B29C 66/9241* (2013.01); *B65B 3/003* (2013.01); *B65B 7/14* (2013.01); *B65B 51/10* (2013.01); *B65B 57/145* (2013.01); *G01G 17/04* (2013.01); *G01G 17/06* (2013.01); *B29C 65/04* (2013.01); *B29C 65/06* (2013.01); *B29C 65/08* (2013.01); *B29C 65/14* (2013.01); *B29C 65/1412* (2013.01); *B29C 65/1425* (2013.01); *B29C 65/18* (2013.01); *B29C 65/30* (2013.01); *B29C 66/71* (2013.01); *B29C 66/81422* (2013.01); *B29C 66/8242* (2013.01); *B29C 66/8244* (2013.01); *B29C 66/83221* (2013.01); *B29L 2023/007* (2013.01); *B29L 2031/7148* (2013.01); *Y10T 156/12* (2015.01)

(58) Field of Classification Search
USPC .......... 53/266.1, 284, 284.7; 156/251, 308.4, 156/309.6, 358, 359, 515, 583.1; 251/4–10
See application file for complete search history.

(56) References Cited

U.S. PATENT DOCUMENTS

| | | | | |
|---|---|---|---|---|
| 4,490,598 | A * | 12/1984 | Minney et al. | B29C 65/04 156/358 |
| 4,625,494 | A * | 12/1986 | Iwatschenko et al. | G01G 17/06 53/432 |
| 5,176,028 | A * | 1/1993 | Humphrey | B29C 65/18 374/45 |
| 5,674,741 | A * | 10/1997 | Watanabe et al. | A61M 1/029 141/114 |
| 5,750,971 | A * | 5/1998 | Taylor | B29C 65/04 219/643 |
| 5,881,535 | A | 3/1999 | Gliniecki et al. | |
| 6,712,963 | B2 * | 3/2004 | Schick | A61M 1/0209 210/137 |
| 7,047,709 | B2 * | 5/2006 | Hamilton | B65B 57/06 53/250 |
| 7,059,580 | B1 * | 6/2006 | Gralensk | F16K 7/063 138/119 |
| 2001/0019117 | A1 * | 9/2001 | Schoeb | A61M 39/28 251/65 |
| 2004/0035844 | A1 * | 2/2004 | Wright et al. | B29C 65/04 219/221 |
| 2005/0199339 | A1 * | 9/2005 | Jensen | B29C 65/18 156/304.2 |
| 2006/0018989 | A1 * | 1/2006 | Woods et al. | B29C 65/18 425/392 |
| 2006/0145105 | A1 * | 7/2006 | Ishida et al. | A61M 1/14 251/7 |

FOREIGN PATENT DOCUMENTS

| | | | | |
|---|---|---|---|---|
| EP | 0551813 | A2 * | 7/1993 | ............ B29C 65/04 |
| EP | 0639384 | A2 | 2/1995 | |
| JP | 57018874 | A * | 1/1982 | |
| JP | 9019495 | A | 1/1997 | |
| WO | 0062891 | A1 | 10/2000 | |

* cited by examiner

WELDING DEVICE, USE THEREOF AS A CONTROL VALVE, AND METERING DEVICE

The present application is a Bypass Continuation of International Application No. PCT/EP2011/005155, filed on Oct. 14, 2011, which claims priority from German Patent Application 10 2010 060 401.1, filed on Nov. 8, 2010. The contents of these applications are hereby incorporated into the present application by reference in their respective entireties.

FIELD AND BACKGROUND OF THE INVENTION

The invention relates to a welding device that is configured for sealing welding of thermoplastic hoses and that comprises a pinching device with at least two pinching jaws, of which at least one is movable and between which a hose, which is to be welded, can be pinched, wherein the pinching device has a heating device, which is coupled to a control unit and is configured to heat the hose pinched between the pinching jaws.

Furthermore, the invention relates to an automated metering device for the metered transfer of a medium from a supply container via a connecting hose, which is made of a thermoplastic material, into a target container, wherein the connecting hose can be positioned between at least two pinching jaws of a controllable pinch valve, which is coupled to a control unit, so that a volumetric flow rate of the medium can be controlled by controlling a pinching pressure that is exerted on the connecting hose by the pinch valve at a pinching point.

Finally the invention relates to the use of the aforementioned welding device in conjunction with the aforementioned metering device.

A welding device of the type described is known from the EP 0551813 B1. A metering device as described above is known from the EP 1525138 B1.

There is a strong trend in modern medical and biotech industries away from re-usable containers to single use containers, so-called "disposables." As a rule, all manufacturing, dispensing, storage and application processes of medical and/or biotechnology fluids have to be carried out under aseptic conditions. In the event that re-usable containers are used, this requirement is fulfilled by first sterilizing the fluids and then checking and documenting the achieved sterility. The processes associated with this sequence of steps are technically intricate and cost intensive. They can be largely dispensed with if single use containers, i.e. disposables, which are already delivered in an aseptic condition by the manufacturer, are used. Plastic bags in particular have achieved success on the market as single use containers. They can be manufactured at a low cost, are easy to sterilize, are light in weight and have very little volume in the empty state, making them easy to dispose.

For typical processes both during the manufacture and also the use of medical and/or biotechnology fluids, the metering operations play an important role. These metering operations take place under various circumstances, e.g. during administration of the fluid, during mixing of various fluids or during dispensing of a fluid into commercially available containers. In any case at least one fluid has to be transferred from at least one supply container into at least one target container. Flexible plastic hoses are widely accepted for the purpose of connecting the supply container and target container, each of which is made as a plastic bag.

Under hygienic aspects the coupling of the hose to a container is viewed critically, for which reason the manufacturers usually provide the bags as a single part or by material bonding with the hoses or with whole hose systems. Once the bag is filled, these hoses are permanently closed, typically at their ends, by welding. Closing the hoses by welding has many advantages. First of all, a bag, or more specifically a hose that is closed by welding, is tamper proof. Secondly, the end of the hose is heated by the welding operation, so that an additional sterilization process is carried out at the critical opening point. In principle, the welding operation is possible with any thermoplastic material, such as PVC, PE, PET, PU, etc.

The aforementioned EP 0 551 813 B1 discloses a welding device, in which the hose that is to be welded is pinched between two pinching jaws that are constructed as welding electrodes. The pinching pressure that is constant during the entire process is so high that it completely closes the free lumen of the hose at the pinching point. The pinching jaws together form a capacitor of an electric high frequency oscillating circuit. When the oscillating circuit is actuated at a suitably high frequency, the molecular dipoles of the hose material pinched between the pinching jaws are set into oscillation and, in so doing, heat up the walls of the hose. The heat buildup causes the hose to melt, so that under the constant pinching pressure the pinching jaws squeeze the softened hose material out of the pinching point, so that the initial result is the welding followed by a severing of the welding point. This publication document focuses, in particular, on the tuning of the resonance frequency of the electric oscillating circuit, where this resonance frequency changes through the passive approach of the pinching jaws under the constant pinching pressure owing to the resulting capacitance change of the capacitor.

The aforementioned EP 1 525 138 B1 discloses a metering device, with which a plurality of small bags provided as the target containers can be filled from a large bag functioning as the supply container. The metering, i.e. the control of the volumetric flow rate from the supply container to the target containers, is performed using pinch valves, which pinch the hose connections between the supply container and the target containers between the actively controllable pinching jaws. In so doing, the pinching pressure is varied in a controlled manner, so that the free lumen of the respective hose at the pinching point changes, and the volume flow through the hose at the pinching point can be varied, as required. Following completion of the bag filling operation, the access hose of the respective target bag is closed with a lock clamp and, in addition, can be permanently welded, for example, with the aforementioned welding device. A drawback of this approach is that the welding of the access hoses for the target containers has to be performed in a separate working step, a feature that entails not only higher costs due to the amount of time that is required and the need for an additional welding device but also entails hygienic risks.

OBJECTS AND SUMMARY OF THE INVENTION

An object of the present invention is to further develop a welding device of this type in such a way that a more efficient and hygienically safer welding of target containers, which are filled by way of hoses, can be performed in a more efficient and hygienically safer way.

An additional object of the present invention is to further develop a metering device of the type desired in such a way that the welding of the hoses of the filled target containers can be performed in a more efficient and hygienically safer way.

The first engineering object described above is achieved by supplementing conventional technology in such a manner that the at least one movable pinching jaw is actuable with a controllable, bidirectional actuator, which is coupled to the control unit in such a way that the pinching pressure acting on the hose is adjustable independently of the heating device.

The second engineering object described above is achieved by supplementing conventional technology in such a manner that at least one of the pinching jaws is provided with a heating device, which is coupled to the control unit and which is configured to heat the connecting hose. In other words, the second aforementioned engineering object is achieved through the use of an inventive welding device as a controllable pinch valve of a metering device.

One important feature of the invention is that the pinching pressure, which the pinching jaws of the welding device exert on the pinching point, is variable and is controllable, in particular, in a targeted way. The person skilled in the art will recognize that in this case there is no need to give an explicit pinching pressure specification. As a result, the pinching pressure can also be adjusted indirectly, for example, by an explicit specification of the distance between the pinching jaws or an actuator feed or the like. The prior art provides only the application of a constant pinching pressure, which can be achieved, in particular, with a passive element, such as, for example, a clamping compression spring. In contrast, the present invention provides that at least one of the pinching jaws be provided with a controllable actuator that is, for example, electrically, pneumatically, hydraulically or magnetically operable. Important is that the actuator can be controlled bidirectionally. That is, the actuator can be actuated not only to raise the pinching pressure but also to lower the pinching pressure. In this case the term "actuator" is to be construed in a broad sense and includes, in particular, also systems comprising a plurality of unidirectionally working, but antagonistically interacting setting elements.

Furthermore, it is important that the actuation of the actuator can take place independently of the heating device. If in the state of the art a change in the distance between the pinching jaws was solely due to the hose material melting at a constant pinching pressure, then the present invention provides that the pinching pressure can be adjusted, as required, in particular, indirectly by way of the distance between the pinching jaws, independently of the heating device and, in particular, when the heating device is inactive. This arrangement allows the free lumen of the pinched hose to be actuated between a maximum opening state and a completely closed state, so that a welding process is not absolutely necessary.

Just like the welding device known from the prior art, the welding device according to the invention has the ability to raise the temperature of the hose material up to at least its softening temperature. In this case the pinching pressure, which is high enough to completely close the lumen of the hose, can be actuated. In other words, the pinching device according to the invention, can be used, independently of one another, as a controllable pinch valve and can be used to permanently weld the hose at the pinching point.

Consequently an additional subject matter of the present invention is the corresponding application of the inventive welding device as a controllable pinch valve of an automated metering device, through which a medium can be transferred in a metered manner into a container from a supply container through a connecting hose, which is pinched between the pinching jaws of the welding device and is made of a thermoplastic material.

With respect to the metering device according to the invention, another important feature is the possibility of heating the pinched connecting hose using a heating device, which is assigned to at least one of the pinching jaws. In this case it has to be possible to raise the temperature up to at least the softening temperature of the connecting hose. In other words, the control valve, which is anyway present in metering devices of this type, is expanded to include the additional capability of permanently welding the pinched hose.

The present invention makes it possible to integrate the closing operation by welding into the metering operation, irrespective of whether in the course of dispensing, mixing or using or the like. In particular, the use of an additional device is not necessary. Even an additional working step, in particular, with the inclusion of manual process steps, is not necessary. The advantages with respect to cost savings and improvement in the hygienic safety are substantial.

The specific configuration of the heating device, with which the pinched hose can be heated, is of secondary importance to the present invention. For example, the hose can be heated directly by generating a high frequency electric field between the pinching jaws. In this case the frequency of the electric field is adjusted to a resonance frequency of the molecular dipoles of the hose material. As an alternative, the hose can be heated directly by heating the pinching jaws, which pinch the hose, using, for example, an integrated resistance heater. The pinching jaws can also be designed as friction welding heads or ultrasonic welding heads that generate microscopic relative movements in the pinched hose and, as a result, produce heat generating friction. Furthermore, use of a heat buildup through radiation, for example, infrared radiation or microwave radiation, is also possible.

Preferably the inventive arrangement provides that the control unit is configured
  to control during a metering operation a volume flow of the medium through the connecting hose when the heating device is in the inactive state in that the pinching pressure, which is exerted on the connecting hose by the pinching jaws, is controlled, as required, and to activate the heating device following completion of the metering operation and to weld the connecting hose by application of a pinching pressure that closes the connecting hose.

With respect to the resulting metering device this means that the heating device is optimally suited and the control unit is optimally configured to heat, following completion of a metering operation, the connecting hose by application of a pinching pressure, which closes the connecting hose, to such an extent that the connecting hose is permanently closed by welding.

A preferred further development of the welding device according to the invention provides that at least one of the pinching jaws has a cutting device, which is coupled to the control unit and which is configured to sever the hose. With respect to the metering device according to the invention this means that preferably at least one of the pinching jaws has a cutting device, which is coupled to the control unit and which is configured to sever the connecting hose. For example, the cutting device can comprise a movable cutting blade.

Especially when the welding device according to the invention is used as described, the provision of a cutting device allows the connecting hose to be severed at the welding point following completion of the welding operation. For this purpose the control unit of the metering device according to the invention is configured preferably to actuate, upon completion of the welding operation, the cutting device for the purpose of severing the connecting hose. In other words, it is preferably provided that the pinched hose be severed at the welding point after said hose has been welded. This arrangement allows each individual bag that is filled to be reliably and permanently closed and then further processed separately, for example, sold. As an alternative to severing the hose using a cutting blade, the hose can also be melted by raising its temperature even more until the severance has taken place.

Additional features and advantages of the invention will be apparent from the following detailed description and the accompanying drawings, which illustrate by way of example some preferred embodiments of the invention.

BRIEF DESCRIPTION OF THE DRAWINGS

The drawings show in

DETAILED DESCRIPTION OF EXEMPLARY EMBODIMENTS

Figure 1:
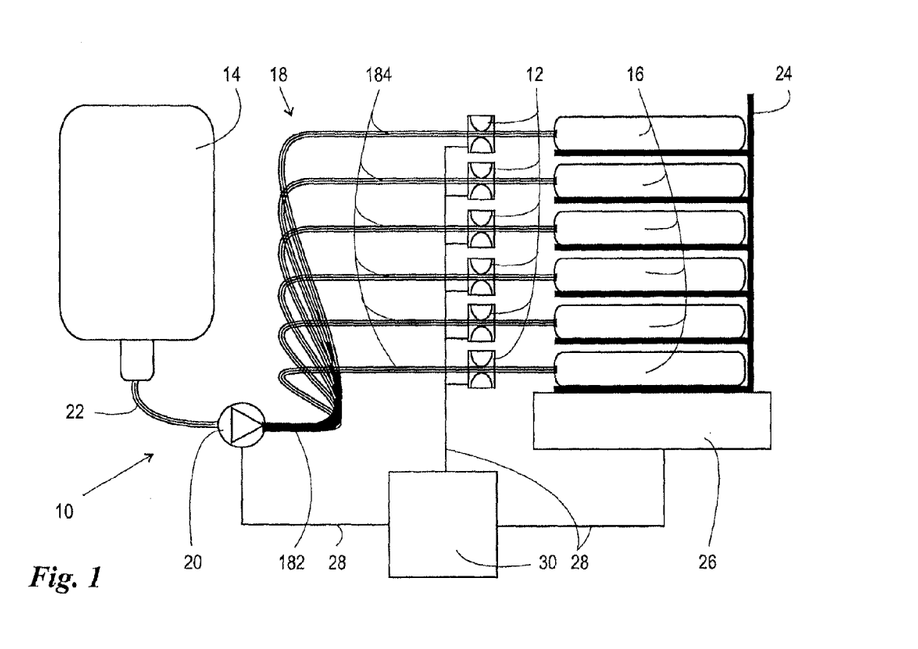
FIG. 1: a metering device according to the invention.

FIG. 1 shows a schematic representation of a metering device, in which the welding devices, designed according to the invention, are used as control valves. Such devices, which lend themselves well to both controlling a volume flow through a hose as well as to welding the hose to close it, are referred to below as welding valves 12.

A purpose of the metering device 10 is to dispense a metered fluid from a large volume supply container 14 into a plurality of target containers 16 of smaller volume. An associated requirement is that the quantity that is to be dispensed respectively to the target containers must be adhered to exactly. The target containers 16 are constructed as flexible plastic bags that are connected, preferably as one piece or by material bonding, to a connecting hose system 18. The connecting hose system 18 in the illustrated embodiment consists of a common hose coupling 182 that splits up into a plurality of individual hoses 184. The common hose coupling 182 is connected to the output of a pump 20. Each individual hose 184 is connected to its assigned target bag 16. Upstream of its connecting point with the respective target bag 16, each connecting hose 184 is pinched between the pinching jaws of a welding valve 12 according to the invention. The pump 20 has an output, to which the common hose coupling 182 of the hose system 18 is attached. The input side of the pump is connected to the supply container 14 through an additional connecting hose 22.

The target bags 16 in the illustrated embodiment are stored on a stacking shelf 24, which in turn is disposed on a balance 26. The balance 26, the welding valves 12 and preferably, as shown in the illustrated embodiment, also the pump 20 are connected to a control unit 30 through control lines 28. The control unit 30 receives weighing signals from the balance 26 and sends, according to the specified rules, the control commands to the welding valves 12 and preferably to the pump 20. The rules of procedure, according to which the evaluation of the weighing signals and the actuation of the welding valves 12 and the pump 20 are executed, are stored in the control unit 30, preferably as software. A typical process sequence for the illustrated metering device could run as follows:

In the initial state, i.e. when all of the hose connections are established, as shown and explained above, and the individual connecting hoses 184 are pinched between the pinching jaws of the welding valves 12, all of the welding valves 12 are activated to "close." That is, their pinching jaws are brought so far together that the lumen of the pinched connecting hose 184 is completely closed. In this state a volume flow through the connecting hose system 18 is not possible. Prior to the start of the actual metering operation, the balance 26 is tared to a base value, preferably set to "zero." Then the pump 20 is started. In this respect an air venting hose, which is not shown in FIG. 1, can be provided; and the air that may be found in the connecting hose system 18 can be blown out through the air venting hose. In order to fill a first target bag 16, for example, the target bag 16, shown at the very bottom in FIG. 1, the corresponding welding valve 12 is opened. That is, the pinching jaws of the welding valve are pulled so far apart that at least a partial lumen of the corresponding connecting hose 184 is released; and a volume flow of the metered fluid from the supply container 14 into the active target bag 16 is enabled. During the bag filling operation, the weight increase of the entire arrangement positioned on the balance 26 is measured in short time intervals, preferably almost continuously; and the measurement results are reported to the control unit 30. This control unit regulates the volumetric flow rate by suitably controlling the active welding valve 12. In this respect the person skilled in the art is familiar with the typical control algorithms for implementing a gravimetric metering procedure using a control valve. At the end of the bag filling operation the active welding valve 12 is closed again. That is, the pinching jaws of the welding valve are brought so far together that the lumen of the corresponding connecting hose 184 is completely closed again.

In the next step of the process, the heating device of the active welding valve is activated. This arrangement allows the connecting hose 184 to be heated at least up to its softening temperature; and at the same time the pinching pressure, exerted on the connecting hose by the pinching jaws of the welding valve 12, is maintained. In this case it is not absolutely necessary that the pinching pressure be held exactly constant. Depending on the choice of hose material, wall thickness, cross section, heating procedure, etc., a variation of the pinching pressure, for example, as a function of the temperature or the material softening, is also conceivable. The only crucial factor is that the pinching pressure be not reduced to such an extent that the lumen of the hose opens again. The softening of the material produces a weld. That is, the inner walls of the connecting hose 184 that are pinched together are connected by material bonding. Then the connecting hose 184 of the target bag 16 that has just been filled is permanently closed. Finally the filled target bag 16 can be severed, as a function of the specific configuration of the welding valve 12, from the rest of the hose system 184 by severing the generated welding point.

Thereafter the process described above for a single target bag 16 is repeated in succession for the rest of the target bags 16. Each new bag filling operation can be introduced with a re-taring of the balance 26. The pump 20 can run continuously or can be started again for each new bag filling operation and then stopped again after the bag filling operation. All of the essential parameters of the bag filling operation are stored preferably by the control unit 30 and can be printed out by an attached printer, for example, as adhesive labels for the individual bags.

Figure 2A:
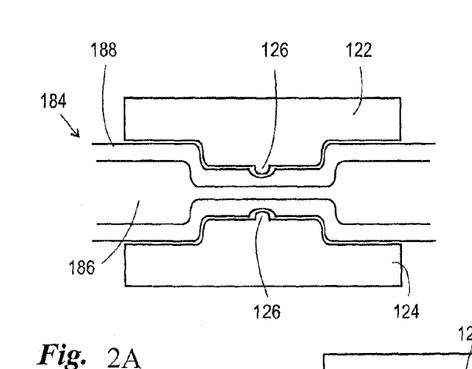
FIG. 2A: an embodiment of a welding valve/pinch valve in a first position.
Figure 2B:
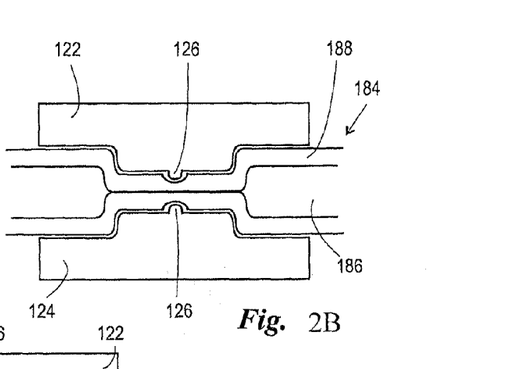
FIG. 2B: an embodiment of the welding valve/pinch valve of FIG. 2A in a second position.
Figure 2C:
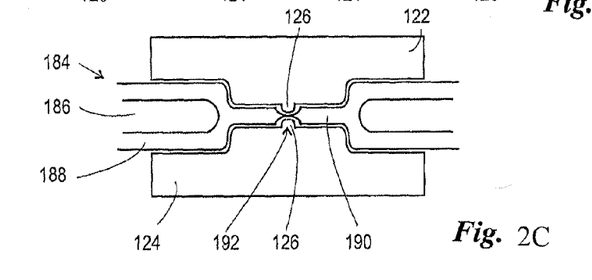
FIG. 2C: an embodiment of the welding valve/pinch valve of FIG. 2A in a third position.

FIGS. 2A-2C provide schematic representations of an inventive welding valve 12 in three different working phases. In this embodiment a connecting hose 184 is pinched between the pinching jaws 122 and 124 of the welding valve. FIG. 2A shows a working phase, in which the pinching jaws 122, 124 are brought so far together that even though the free lumen 186 of the connecting hose 184 between the pinching jaws 122, 124 is obviously constricted, it still allows a (reduced) volume flow through the connecting hose 184. In FIG. 2B the pinching jaws 122, 124 are brought even closer together, so that the interior sides of the hose walls 188 touch each other. That is, the lumen 186 of the hose is completely closed in the region between the pinching jaws 122, 124. In this state a volume flow through the connecting hose 184 is not possible. However, the lumen 186 can be opened again by opening, i.e. pulling apart, the pinching jaws 122, 124. Finally FIG. 2C shows a phase, in which the pinching jaws 122, 124 are brought together to the maximum extent; and the heating device, which is not shown separately in FIGS. 2A-2C, is activated. The heat buildup in the connecting hose 184 to at least its softening temperature causes the hose walls 188 that have made contact with one another to be welded to one another. The result is a welding point (i.e. one or more point locations, lines, areas or volumes), which is provided with the reference numeral 190 and at which the lumen 186 of the connecting hose 184 is permanently closed due to the material bonding of its hose walls 188.

In the depicted embodiment the pinching jaws 122, 124 have a cutting projection 126 at opposite locations. Between the cutting projections 126 the connecting hose 124 is compressed to a greater extent than in the region of the rest of the welding point 190. This arrangement allows the softened hose material to flow between the cutting projections 126 to the external environment, with the result that the cutting point 192 is completely severed. This process can be facilitated by configuring the heating device in such a way that the hose material between the connecting projections 126 heats up faster than between the other regions of the pinching jaws 122, 124.

Figure 3:
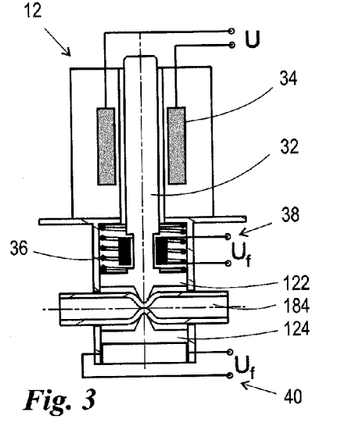
FIG. 3: a first embodiment of a magnetically actuated welding valve/pinch valve.

In FIG. 3 a first embodiment of a welding valve according to the invention is shown in more detail. In this embodiment the function of the welding valve as a control valve is implemented by a spring-biased electromagnetic drive. Connected to the pinching jaw 122, which may be found at the top in FIG. 3, is a tappet 32, which is constructed preferably as a soft iron core and which is surrounded by a coil 34. The coil 34 is connected to a controllable direct voltage source, with which the lift of the tappet 32 and, with it, the pinching pressure, which the pinching jaw 122 in interaction with the pinching jaw 124, which may be found at the bottom in FIG. 3, exerts on the pinched hose 184, can be controlled. In the depicted embodiment the pinching jaw 122 is spring biased with a spring 36 in such a way that when the coil 34 is de-energized, the valve is switched to "closed." That is, the electromagnet 32/34 acts antagonistically to the spring 36.

Furthermore, two different heating devices are shown in FIG. 3.

The pinching jaw 122, which may be found at the top in FIG. 3, is an electromagnetic vibration heating device 38; and the pinching jaw 124, which may be found at the bottom in FIG. 3, is assigned a piezoelectric vibration heating device 40. The details of these design variants shall be described below in conjunction with the FIGS. 8 and 9. It should be noted that the illustrated heating devices 38, 40 are preferably not implemented, as suggested in FIG. 3, jointly in a welding valve 12. Rather, preferably only one sort of heating device is realized in a welding valve 12. At the same time it is possible to both equip each of the two pinching jaws 122, 124 with a heating device and also to provide only one of the pinching jaws 122, 124 with a heating device. When confronted with a specific problem, the person skilled in the art can easily solve such questions relating to the layout.

Figure 4:
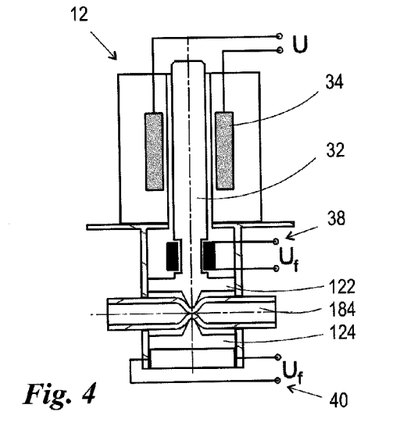
FIG. 4: a second embodiment of a magnetically actuated welding valve/pinch valve.

FIG. 4 shows a modification of the welding valve 12 from FIG. 3. In this embodiment there is no bias spring 36. Therefore, when this welding valve 12 is in the de-energized state, it will move automatically into the "open" state due to the intrinsic elasticity of the pinched hose. Moreover, the aforesaid with respect to the welding valve 12 in FIG. 3 also applies.

Figure 5:
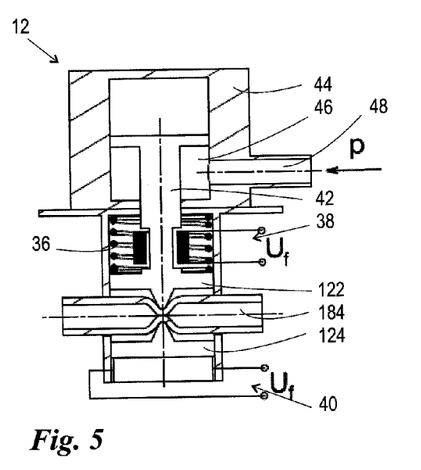
FIG. 5: a first embodiment of a pneumatically/hydraulically actuated welding valve/pinch valve.

FIG. 5 shows an alternative implementation of the control valve function of the welding valve according to the invention. The pinching jaw 122, which may be found at the top in FIG. 5, merges into a piston 42, which forms a pressure chamber 46 in a housing 44. The pressure chamber 46 is connected to a pressure line, through which a pressure medium, for example, a hydraulic fluid for realizing a hydraulic system or a compressed gas for realizing a pneumatic system, can be conveyed into the pressure chamber 46. When the pressure in the pressure chamber 46 is increased, the piston 42 is raised upwards against the pressure of the spring 36 that prestresses the pinching jaw 122 in the "closed" direction. That is, the pinching pressure on the pinched hose is reduced. Reduction of the pressure in the pressure chamber 46 lowers the lift force acting on the spring 36, so that the pinching jaw 122 descends. Hence, in a depressurized state the welding valve 12 is in its "closed" position. Since this embodiment does not offer the possibility of increasing the pinching pressure hydraulically or pneumatically by way of the baseline pressure of the spring 36, the spring 36 is configured preferably so strong that it alone suffices to guarantee a total lumen closure of the pinched hose as well as a pinching pressure necessary for the welding operation. Moreover, the aforesaid with respect to the welding valve 12 in FIG. 3 also applies.

Figure 6:
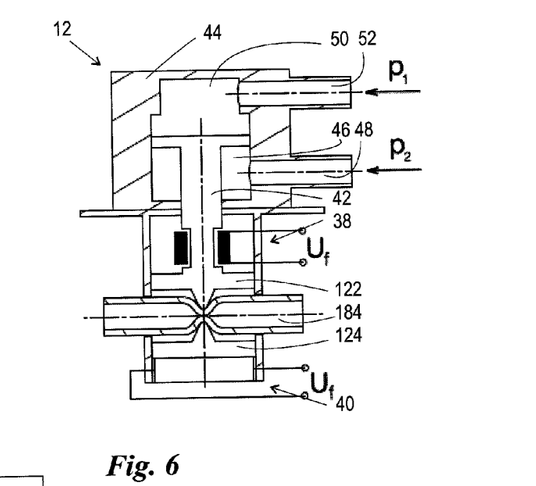
FIG. 6: a second embodiment of a pneumatically/hydraulically actuated welding valve/pinch valve.

FIG. 6 shows a modification of the welding valve 12 from FIG. 5. In this embodiment there is no bias spring 36, so that the piston 42 has to be actuated pneumatically and/or hydraulically in both the "closed" direction and also in the "open" direction. For this purpose there is an additional pressure chamber 50 above the piston 42, which is connected to a second pressure line 52. As a result, the pinching pressure, acting on the pinched hose, is directed essentially by the differential pressure into the pressure chambers 46 and 50. Moreover, the aforesaid with respect to the welding valve in FIG. 5 also applies.

Figure 7:
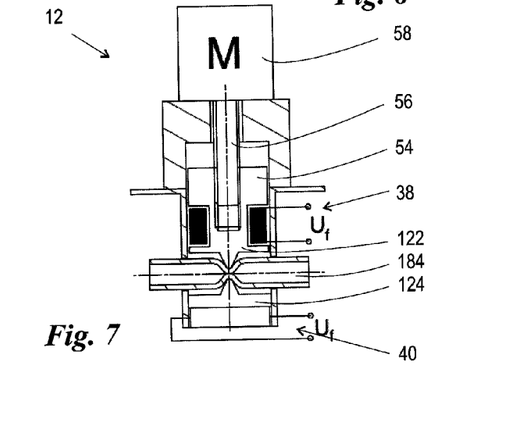
FIG. 7: an embodiment of a motor actuated welding valve/pinch valve.

FIG. 7 shows an embodiment of the inventive pinch valve 12, in which the control valve function is implemented with a mechanical spindle drive. To this end the pinching jaw 122, which may be found at the top in FIG. 7, is connected to a threaded nut 54 having an inside thread, in which a threaded spindle 56 is disposed. This threaded spindle in turn can be rotated about its longitudinal axis by a motor 58. This embodiment does not provide an initial stress, for example, using a bias spring. However, in the event of a correspondingly coarse pitch design of the thread of the threaded nut 54 and the threaded spindle 56, a mechanical tensioning may also be practical. Moreover, the aforesaid with respect to the welding valve 12 in FIG. 3 also applies.

Figure 8:
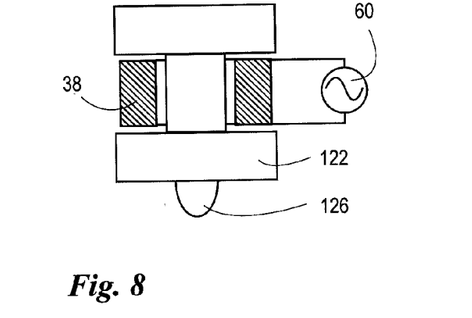
FIG. 8: a schematic representation of clamping heads/welding heads that are heated by electric resistance.

FIG. 8 is a highly simplified schematic representation of an electromagnetic vibration heater, which can be assigned to a pinching jaw 122 of a welding valve 12 according to the invention. In this depicted embodiment the pinching jaw 122 has a soft iron base plate or a permanent base plate that is surrounded by a coil 38. The coil 38 is connected to an alternating current source 60, so that when the coil 38 is supplied with current, an axial vibration of the pinching jaw 122 is generated. This vibration, which is pushed away from the material of a pinched hose, generates friction in this hose, so that the hose heats up. As soon as the hose heats up sufficiently, the material softens; and this material softening in turn results in a welding of the pinched hose 184 at an adequately high baseline pressure. As an alternative, the pinching jaw 122 could also be mounted rotatably about its longitudinal axis; and its base plate could have magnetic segments which are spaced apart from one another in the circumferential direction in the manner of an electric motor. These magnetic segments are surrounded by a suitable coil arrangement. A suitable actuation of the current feed permits a rotation or rotative vibration of the pinching jaw 122 to be generated; and the pinched hose can be heated through the resulting friction.

Figure 9:
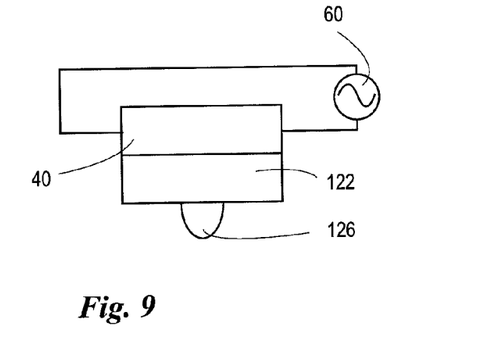
FIG. 9: a schematic representation of a magnetically operated clamping head/friction welding head.

FIG. 9 shows an alternative design variant for heating a pinched hose by friction. In this embodiment the pinching jaw 122 is mounted on a piezoelectric base plate, to which a suitable alternating voltage is applied. The piezoelectric effect causes the piezoelectric base plate to expand and to shrink, so that the result is a vibration of the pinching jaw 122. Depending on the specific configuration of the piezo base plate 40, a number of diverse vibrations of the pinching jaw 122, for example axial, lateral or rotative, can fulfill the objective.

Figure 10:
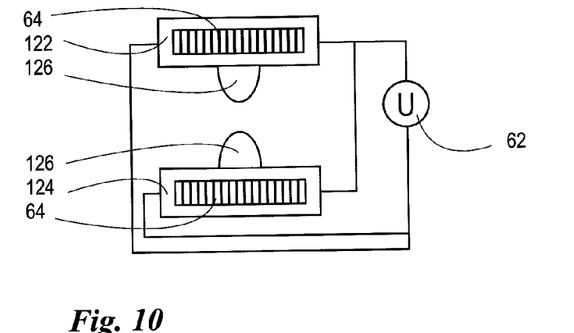
FIG. 10: a schematic representation of a motor operated clamping head/friction welding head.

FIG. 10 shows an alternative heating device, in which the pinching jaws 122, 124 are provided with resistance heating elements 64. These resistance heating elements are connected to a direct or alternating voltage source and heat up in a manner known in the prior art. If the material of the pinching jaws 122, 124 is properly chosen with a preferably high thermal conductivity, for example, copper or brass, then the electrically generated heat can be easily transferred in a targeted way to the pinched hose.

Figure 11:
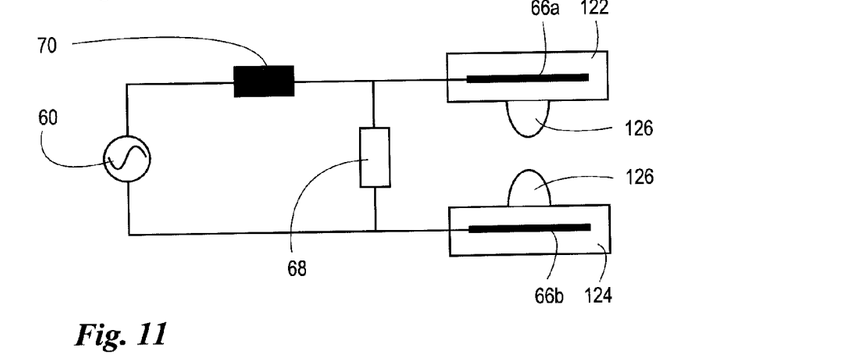
FIG. 11: a schematic representation of electric HF (high frequency) clamping heads/welding heads.

FIG. 11 shows an electric high frequency heating device, in which the pinching jaws 122, 124 act as the "plates" 66a, 66b of an electric parallel plate capacitor. The capacitor is an essential part of an electric oscillating circuit, which can comprise additional electric elements, such as an ohmic resistor 68 and a coil 70. The electric oscillating circuit is excited, preferably in resonance, by an alternating voltage source. If the resonance frequency of the oscillating circuit is tuned to the resonance frequency of the molecular dipoles in the wall material of the hose, then these molecular dipoles can be excited to oscillate by way of the alternating field applied to the capacitor, a feature that becomes apparent in the heat buildup of the wall material.

Figure 12:
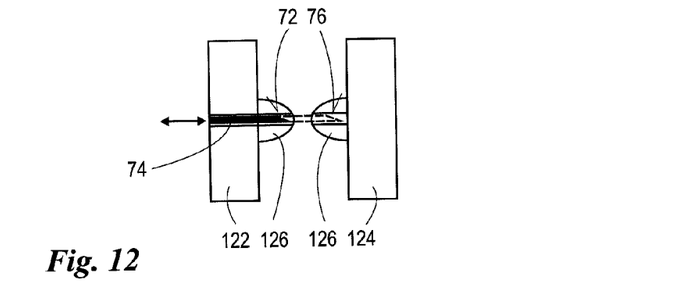
FIG. 12: a schematic representation of an integrated hose-cutting device.

FIG. 12 shows a preferred further development of the invention that is independent of the implementation of the control valve function and the implementation of the heating function. The pinching jaw 122, which is shown on the left in FIG. 12, has an axial cutting channel 74. The cutting channel 74 conceals an axially movable cutting blade 72. This cutting blade can slide axially under influence of a drive (not illustrated) and, in particular, between a protective position, which is shown by a blade 72, which is colored in black in FIG. 12, and a cutting position, which is shown as a blade 72 bounded by dashed lines in FIG. 12. In the protective position the cutting edge of the cutting blade 72 is retracted into the pinching jaw 122. In the cutting position the cutting edge is pushed beyond the front edge of the pinching jaw 122 and is received preferably in a corresponding receiving channel 76 of the opposite pinching jaw 124. The person skilled in the art can see that a hose (not shown in FIG. 12), which is pinched between the pinching jaws 122, 124, is severed in this cutting position. The severing operation takes place preferably after completion of the welding operation of the pinched hose in the center of the resulting welding point.

The embodiments discussed in the specific description and shown in the figures are only illustrative exemplary embodiments of the present invention. In light of the present disclosure the person skilled in the art is provided with a broad spectrum of possible design variations. In particular, the shape of the pinching jaws 122, 124 can be adjusted to the desired shape of the welding point and can deviate significantly from the shapes that are shown in the present disclosure. Even the specific choice of the implementation of the control valve function is just as immaterial for the invention as the specific implementation of the heating or welding function respectively. Furthermore, the metering function according to the invention can be configured in a different way than shown, in particular with more or less target containers 16 and/or more supply containers 14 and with additional or alternative components, which are not illustrated. For example, the volume flow from the supply container(s) 14 to the target bags 16 can also take place without the use of a pump 20, for example, by applying pressure to the target container(s) 16 or can be gravity driven. Instead of a stacking shelf 24, in which the target bags 16 are arranged one above the other, it is possible to use an arrangement, in which the target bags are arranged side by side, for example, in a rack.

In other words, the above description of various embodiments has been given by way of example. From the disclosure given, those skilled in the art will not only understand the present invention and its attendant advantages, but will also find apparent various changes and modifications to the structures and methods disclosed. The applicant seeks, therefore, to cover all such changes and modifications as fall within the spirit and scope of the invention, as defined by the appended claims, and equivalents thereof.

What is claimed is:

1. An automated metering device comprising:
a metering device,
a control unit in communication with the metering device,
a welding device configured to sealingly weld a thermoplastic hose, said welding device comprising a pinching device with at least two pinching jaws, of which at least one of the pinching jaws is movable and between which pinching jaws the hose is arranged to be pinched and welded,
   wherein the pinching device comprises a heating device, which is coupled to the control unit and which is configured to heat the hose while the hose is pinched between the pinching jaws, and
   wherein the at least one movable pinching jaw is configured to be actuated by a bidirectional actuator, which is coupled to the control unit such that pinching pressure exerted on the hose is adjusted independently of the heat from the heating device acting on the hose, and
a medium arranged for transfer metered in accordance with the metering device into a target container from a supply container through the hose,
   wherein the control unit is configured:
      to control, during a metering operation, a volume flow of the medium through the hose when the heating device is in an inactive state, such that the pinching pressure exerted on the hose by the pinching jaws, is controlled in accordance with the control unit, and
      to activate the heating device to weld the hose by application of the pinching pressure, which closes the hose, following completion of the metering operation.

2. The welding device, as claimed in claim 1, wherein at least one of the pinching jaws comprises a cutting device to which the control unit is coupled and which is configured to sever the hose.

3. The welding device, as claimed in claim 2, wherein the cutting device comprises a movable cutting blade.

4. The metering device as claimed in claim 1, further comprising a cutting device, wherein the control unit is further configured:
   to activate the cutting devise to cut the hose at the welding point following completion of the welding operation.

5. The device as claimed in claim 1, wherein the metering device comprises a balance that outputs weighing signals to the control unit that control the volume flow of the medium through the hose.

6. A device, comprising:
at least one metering and welding valve with at least two cooperating jaws configured to hold, constrict and release a hose,
a heat source incorporated into the valve and configured to heat the hose held between the jaws in accordance with a heat setting,
a weighing scale, and
a control unit in communication with the scale and the valve, and configured to output a first control signal and a second control signal,
   wherein an extent of constriction of the valve is variable in accordance with the first control signal, and an extent of heat output by the heat source is variable in accordance with the second control signal, and
   wherein settings for the first control signal and for the second control signal are mutually arranged to activate the heat source only when the valve is constricted.

7. The device as claimed in claim 6, wherein the valve is selected from the group consisting of:
an electromagnetic drive, a hydraulic drive, a pneumatic drive and a mechanical spindle drive.

8. The device as claimed in claim 7, wherein the valve is spring-biased.

9. The device as claimed in claim 6, wherein the heat source is selected from the group consisting of:
   an electromagnetic vibration heating device, a piezoelectric vibration device, a resistive heating device, and an electric high frequency heating device.

* * * * *